(12) United States Patent
Bjorkman et al.

(10) Patent No.: US 7,632,254 B1
(45) Date of Patent: Dec. 15, 2009

(54) DEVICE FOR SPLITTING THE TUBULAR BODY OF A CATHETER OR SHEATH

(75) Inventors: Bradford A. Bjorkman, Elk River, MN (US); Daniel J. Potter, Stillwater, MN (US); Donald G. Goblish, Cologne, MN (US)

(73) Assignee: Pacesetter, Inc., Sylmar, CA (US)

( * ) Notice: Subject to any disclaimer, the term of this patent is extended or adjusted under 35 U.S.C. 154(b) by 251 days.

(21) Appl. No.: 11/338,031

(22) Filed: Jan. 23, 2006

(51) Int. Cl.
*A61M 5/14* (2006.01)
*F16K 1/48* (2006.01)
(52) U.S. Cl. .................. 604/256; 251/369; 604/164.05
(58) Field of Classification Search ............... 604/160, 604/164.04–164.05, 167.04, 246, 256, 164.06; 83/397; 251/331, 369
See application file for complete search history.

(56) References Cited

U.S. PATENT DOCUMENTS

| 4,412,380 A | * | 11/1983 | Kish | ..................... 30/92 |
| 5,312,355 A | * | 5/1994 | Lee | ..................... 604/160 |
| 5,620,020 A | * | 4/1997 | Collins | ..................... 137/318 |
| 5,669,883 A | * | 9/1997 | Scarfone et al. | ......... 604/164.11 |
| 6,159,198 A | * | 12/2000 | Gardeski et al. | ............. 604/523 |

OTHER PUBLICATIONS

"Pacing Lead Stabilizer", *Pressure Products, Inc.*, Jul. 2004; (abstract) http://www.pressure-products.com/.
"Braided Sheath Slicer", *Pressure Products, Inc.*; (abstract) http://www.pressure-products.com/.
"RAPIDO Dual-Catheter System", *Guidant*, Jul. 2004; (abstract) http://www.guidant.com/products/ProductTemplates/CRM/RAPIDO_CUTAWAY_INTRO.shtml.
"Attain™ Lef-heart Lead Delivery Systems", *Medtronic, Inc.*, Jul. 2004; (abstract) http://www.medtronic.con/hg/physician/attain.html.

* cited by examiner

*Primary Examiner*—Kevin C Sirmons
*Assistant Examiner*—Bradley J Osinski

(57) ABSTRACT

The present invention is a tool coupled to a hemostasis valve and adapted to slit/split a tubular body of a catheter or sheath to facilitate the removal of the tubular body from about a medical device extending through the hemostasis valve and tubular body. The tool comprises a conical barrel portion supporting one or more radially outward extending blades. The tool also comprises a stabilizing component for preventing displacement between the tool and medical device when the tubular body is being removed from about the medical device.

12 Claims, 6 Drawing Sheets

DEVICE FOR SPLITTING THE TUBULAR BODY OF A CATHETER OR SHEATH

FIELD OF THE INVENTION

The present invention relates to devices for, and methods of, working with a catheter or sheath. More specifically, the present invention relates to devices for, and methods of, splitting the tubular body of a catheter or sheath.

BACKGROUND OF THE INVENTION

Some medical procedures utilizing catheter or sheath systems require that the tubular bodies of such systems be split in order to allow the removal of the tubular bodies from a patient. For example, catheter and sheath systems are utilized to deliver a left ventricular ("LV") lead of a cardiac resynchronization therapy ("CRT") system into the coronary sinus of a patient for implantation. In order to allow the tubular body to be removed off the implanted lead and from within the patient once implantation is complete, the tubular body must be longitudinally split.

To facilitate the slitting/splitting of a tubular body, several companies offer separate dedicated slitting/splitting tools. For example, Pressure Products, Inc. of 1861 N. Gaffey Street, San Pedro, Calif. 90731 offers the models PLS-07, PLS-09, SLT-07 and SLT-09 slitting/splitting tools. In use, these tools are aligned with and placed onto the lead after a hemostasis valve at the proximal end of the tubular body is manually split. The slitting/splitting tool is then slid over the lead until the tool's tip encounters the tubular body. The tool is then secured to the lead and the tubular body is withdrawn from the patient and over the tool, thereby slitting/splitting the tubular body and allowing the tubular body to be removed off the lead without inadvertent lead dislodgement. Medtronic, Inc. of 710 Medtronic Parkway, Minneapolis, Minn 55432-5604 and Guidant Corporation of 111 Monument Circle, Indianapolis, Ind. 46204-5129 offer similar slitting/splitting tools.

Because the aforementioned slitting/splitting tools must be aligned with, placed on, and secured to the lead extending through the tubular body, the tools unnecessarily complicate the tubular body removal process. Accordingly, there is a need in the art for a device for, and a method of, slitting/splitting a tubular body of a catheter or sheath that reduces the complication associated with such a procedure.

BRIEF SUMMARY OF THE INVENTION

The present invention, in one embodiment, is a tool coupled to a hemostasis valve and adapted to slit/split a tubular body of a catheter or sheath to facilitate the removal of the tubular body from about a medical device extending through the hemostasis valve and tubular body. The tool comprises a conical barrel portion supporting a radially outward extending blade.

In one embodiment, the tool is integrally formed as part of the hemostasis valve. In one embodiment, the tool is coupled to the hemostasis valve via chemical, sonic, laser, or heat welding. In one embodiment, the tool is coupled to the hemostasis valve via a mechanical coupling arrangement.

In one embodiment, the tool further comprises a slot extending longitudinally along the tool. The slot receives the medical device when the tool is being mounted on the hemostasis valve.

In one embodiment, the blade comprises a slitting/splitting edge that extends along a route that is generally oblique to a longitudinal axis of the tool. The distance between the slitting/splitting edge and a longitudinal axis of the tool increases as the slitting/splitting edge is followed rearwardly from a front tip of the tool.

In one embodiment, the blade comprises a slitting/splitting edge that extends along a route that is generally perpendicular to a longitudinal axis of the tool. The blade further comprises a guard that longitudinally extends along a radially outward border of the blade.

In one embodiment, the tool further comprises a stabilizing component adapted to selectively resist displacement between the tool and the medical device. In one embodiment, the stabilizing component comprises a pad that is displaced inwardly to cause the stabilizing component to engage the medical device. In one embodiment, the stabilizing component comprises the sides of the tool, which are pliable or moveable to allow inward displacement of the sides when squeezed. Squeezing the tool sides inward causes the sides to engage and stabilize the medical device.

The present invention, in one embodiment, is a method of removing a catheter or sheath tubular body from about a medical device extending through the tubular body and a hemostasis valve, wherein the hemostasis valve is coupled to the tubular body via a connective end of the tubular body. In one embodiment, the method comprises detaching the connective end from the hemostasis valve, splitting the connective end, and slitting/splitting the tubular body with a blade coupled to the hemostasis valve. In one embodiment, the method comprises detaching the connective end from the hemostasis valve, and slitting/splitting the connective end and tubular body with a blade coupled to the hemostasis valve.

In one embodiment, the method further comprises causing a stabilizing component to engage the medical device to prevent displacement between the medical device and the hemostasis valve. In one embodiment, the method further comprises providing a tool and coupling the tool to the hemostasis valve, wherein the tool supports the blade. In one embodiment, the method further comprises passing the medical device through a slot longitudinally extending along the tool.

The present invention, in one embodiment, is a hemostasis valve adapted to slit/split a catheter or sheath tubular body. The hemostasis valve comprises a blade and a component adapted to selectively engage a medical device extending through the hemostasis valve. The component, when engaged, prevents displacement between the hemostasis valve and the medical device.

In one embodiment, the hemostasis valve further comprises a conical barrel portion. The blade radially extends from the conical barrel portion.

In one embodiment, the blade comprises a slitting/splitting edge that extends longitudinally along the conical barrel portion. A distance between the slitting/splitting edge and a longitudinal axis of the conical barrel portion increases traveling from a leading tip of the conical barrel portion to a base of the conical barrel portion.

In one embodiment, the blade comprises a slitting/splitting edge that extends radially outward and faces forward. The blade extends between a guide and an outer circumferential surface of the conical barrel portion. The guide extends generally parallel to a longitudinal axis of the conical barrel portion.

In one embodiment, the conical barrel portion is integrally formed with the rest of the hemostasis valve. In one embodiment, the conical barrel portion is coupled to the rest of the hemostasis valve via sonic, chemical, laser or heat welding.

In one embodiment, the conical barrel portion is mechanically coupled to the hemostasis valve. In one embodiment, the conical barrel portion includes a female end that receives a male end of the hemostasis valve in a mechanical friction fit coupling arrangement. In one embodiment, the conical barrel portion includes a male end that is received in a female end of the hemostasis valve in a mechanical friction fit coupling arrangement. In other embodiments, the mechanical connection between the conical barrel portion and the hemostasis valve will be achieved via mechanical connection arrangements other than male/female connection arrangements.

The present invention, in one embodiment, is a method of using a hemostasis valve for slitting/splitting a catheter or sheath tubular body. The method comprises providing a hemostasis valve coupled to a blade and causing the tubular body to slit/split along the blade.

In one embodiment, the method further comprises preventing displacement between the hemostasis valve and a medical device extending through the hemostasis valve. In one embodiment, the method further comprises coupling the blade to the hemostasis valve. In one embodiment, the method further comprises passing the tubular body through a slot prior to coupling the blade to the hemostasis valve.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

The present invention, in one embodiment, is device and method for slitting/splitting a tubular body of a catheter or sheath in a manner that is more efficient and less complicated, as compared to devices and methods previously existing in the art. Specifically, the present invention, in one embodiment, is a hemostasis valve assembly 25 comprising a slitting/splitting tool 30 integrated into or coupled with a hemostasis valve 35. The valve assembly 25 with its slitting/splitting tool 30 is configured to facilitate the removal of a catheter or sheath tubular body extending from the hemostasis valve 35. The valve assembly 25 is advantageous in that the slitting/splitting tool 30 is automatically aligned with, and mounted on, a medical device (e.g., a LV lead of a CRT system, a catheter, etc.) from about which the tubular body must be removed.

Figure 2:
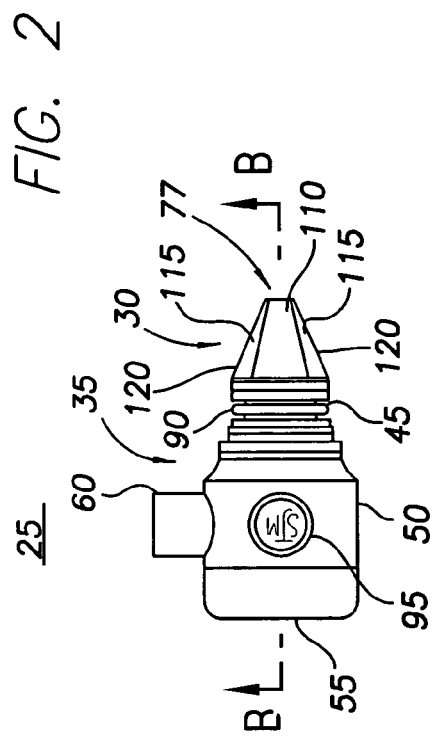
FIG. 2 is a side elevation of the valve assembly depicted in FIG. 1.
Figure 4:
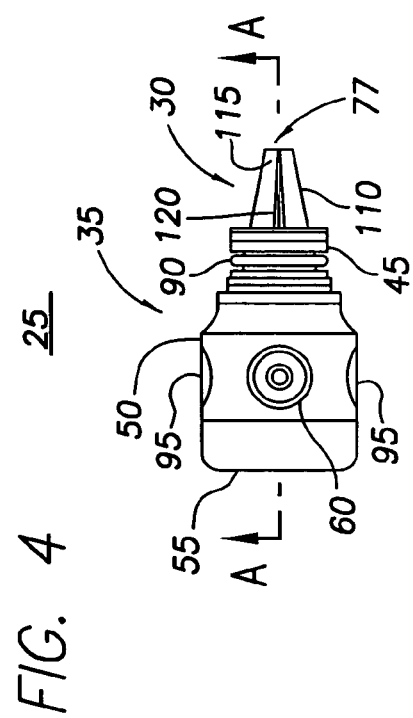
FIG. 4 is a top plan view of the valve assembly depicted in FIG. 1.
Figure 1:
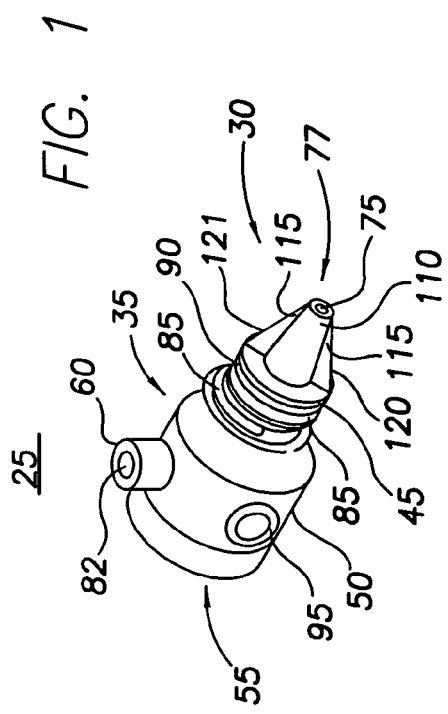
FIG. 1 is an isometric view of a hemostasis valve assembly with an integral slitting/splitting tool.
Figure 3:
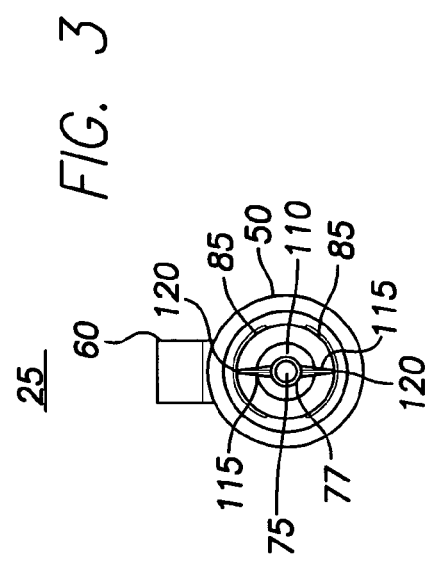
FIG. 3 is an end elevation of the valve assembly depicted in FIG. 1.
Figure 5:
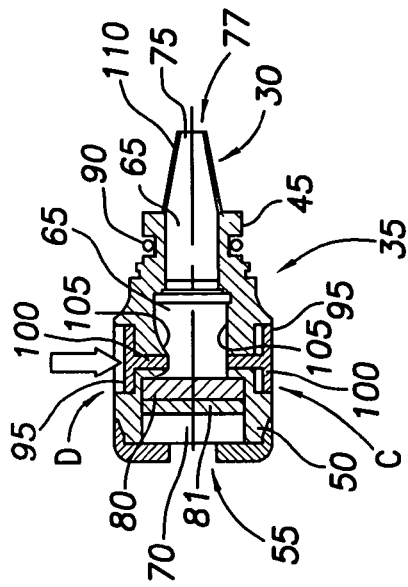
FIG. 5 is a sectional elevation of the valve assembly as taken along section line AA in FIG. 4.
Figure 6:
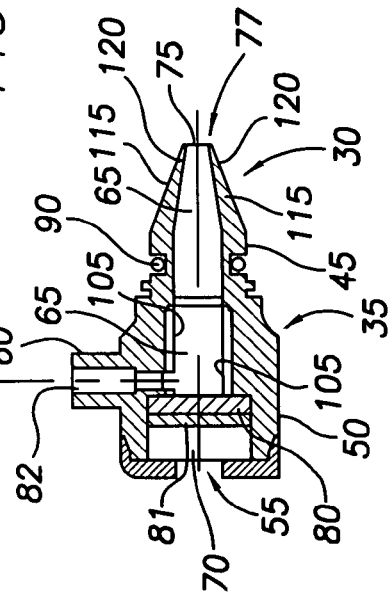
FIG. 6 is a sectional plan view of the valve assembly as taken along section line BB in FIG. 2.

For a discussion of a first embodiment of the subject invention, reference is made to FIGS. 1-6. FIG. 1 is an isometric view of a hemostasis valve assembly 25 with an integral slitting/spitting tool 30. FIG. 2 is a side elevation of the valve assembly 25 depicted in FIG. 1. FIG. 3 is an end elevation of the valve assembly 25 depicted in FIG. 1. FIG. 4 is a top plan view of the valve assembly 25 depicted in FIG. 1. FIG. 5 is a sectional elevation of the valve assembly 25 as taken along section line AA in FIG. 4. FIG. 6 is a sectional plan view of the valve assembly 25 as taken along section line BB in FIG. 2.

As shown in FIGS. 1-6 the hemostasis valve assembly 25 includes a hemostasis valve 35 and an integral slitting/splitting tool 30 extending from a male connective end 45 of the valve 35. The valve 35 includes a cylindrical body 50 that extends between an entry end 55 and the male connective end 45. An optional tap 60 extends perpendicularly from the sidewall of the cylindrical body 50.

As shown in FIGS. 5 and 6, the cylindrical body 50, male connective end 45 and slitting/splitting tool 30 define a first lumen 65 that extends from an opening 70 in the entry end 55 to an opening 75 in the tip 77 of the tool 30. In one embodiment, a sealing mechanism extends across the lumen 65 near the opening 70 in the entry end 55. In one embodiment, the sealing mechanism is a pair of stacked resilient sealing membranes 80, 81 that extend across the lumen 65 near the opening 70 in the entry end 55. In one embodiment, each flexible membrane 80, 81 includes a slit extending across a portion of the membrane 80, 81. In one embodiment, the slits radially offset from each other and intersect at a point along their lengths. In one embodiment, the resilient sealing membranes 80, 81 are formed from a generally resilient, soft polymer material (e.g., silicone, polyether block amides "PEBAX", poly biphenyl compounds "PBC", santaprene, neoprene, latex, etc.). In other embodiments, other membrane configurations or sealing arrangements will be used for the sealing mechanism.

As shown in FIGS. 1 and 5, a second lumen 82 extends perpendicularly from the first lumen 65 through the optional tap 60 where present. The second lumen 82 allows fluids to be entered into or withdrawn from the first lumen As illustrated in FIGS. 1 and 3, in one embodiment, coupling mechanisms are provided for coupling the male connective end 45 to the female connective end of the catheter or sheath tubular body. For example, in one embodiment, the male connective end 45 includes a pair of bayonet-type lock elements 85 for securing the male connective end 45 to a female connective end of a catheter or sheath tubular body such that the male connective end 45 and the slitting/splitting tool 30 are received within the female connective end. In other embodiments, the coupling mechanisms include threads on the male and female connective ends, biased latching arrangements, etc.

As shown in FIGS. 1, 2 and 4-6, in one embodiment, the male connective end 45 also includes an o-ring 90 for sealing the connection between said male and female connective ends. In one embodiment, the o-ring 90 is located on the female connective end. In other embodiments, no o-ring 90 is necessary because one or more portions of the male and/or female connective ends are formed from resilient material to achieve a sealing connection between said male and female connective ends.

A medical device (e.g., a LV lead of a CRT system, a catheter, etc.) can be inserted into the opening 70 in the entry end 55, through slits in the membranes 80, 81, through the first lumen 65 and out the tip opening 75 into the tubular body of the attached catheter or sheath. The membranes 80, 81 seal about the medical device to prevent the backflow of blood or other body fluids through the valve assembly 25.

As indicated in FIGS. 1, 2, 4 and 6, in one embodiment, the cylindrical body 35 employs a medical device stabilizing component. In a first embodiment of the stabilizing component, the stabilizing component includes a pair of opposed pads, depressible sections or buttons 95 that are perpendicularly inwardly displaceable such that a shaft 100 or other portion of each button 95 extends into the first lumen 65 when each button 95 is depressed. As shown in FIG. 6, the first embodiment of the medical device stabilizing component further includes a resilient polymer lining or tube 105 that extends across the inner circumferential surface of the first lumen 65. When a button 95 is not depressed inwardly, the lining 105 biases the button 95 outwardly as depicted at C in FIG. 6. As shown at D in FIG. 6, when a button 95 is depressed inwardly, the lining 105 is forced inward into the first lumen 65 by the shaft 100 or other portion of the button 95. Depressing both buttons 95 inwardly causes the lining 105 to bulge inwardly such that the lining engages the medical device extending through the valve assembly 25. Thus, the first embodiment of the medical device stabilizing component can be used to prevent displacement between the valve assembly 25 and the medical device.

In a second embodiment of the stabilizing component, the sidewalls of the cylindrical body 50 are resiliently pliable such that the sidewalls can be squeezed inwardly. Squeezing the sidewalls of the cylindrical body 50 inwardly brings the inner circumferential surface of the first lumen 65 into engaging contact with the medical device extending through the valve assembly 25. Thus, the second embodiment of the medical device stabilizing component can be used to prevent displacement between the valve assembly 25 and the medical device.

As shown in FIGS. 1, 2 and 4-6, the slitting/splitting tool 30 extends from the distal end of the male connective end 45. In one embodiment, the tool 30 is an integrally molded extension of the connective end 45. In one embodiment, the tool 30 is a separate piece coupled to the connective end 45 via mechanical methods (e.g., bayonet-type connective features, mechanical crimping, etc.) or via fusing methods (e.g., various types of welding including sonic, chemical, heat, laser, etc.).

As illustrated in FIGS. 1, 2 and 4, in one embodiment, the slitting/splitting tool 30 includes a barrel portion 110 and a pair of blades 115 that extend perpendicularly from opposite sides of the outer circumferential surface of the barrel portion 110. The blades 115 extend longitudinally along the length of the barrel portion 110. In one embodiment, the barrel portion 110 is conical and tapers from its widest point at the male connective end 45 to its narrowest point at the tip 77. In one embodiment, the blades 115 taper from their widest points at the male connective end 45 to their narrowest points at the tip 77. Each blade 115 has a sharp cutting edge 120 for slitting/splitting the tubular body of catheter or sheath.

Figure 14:
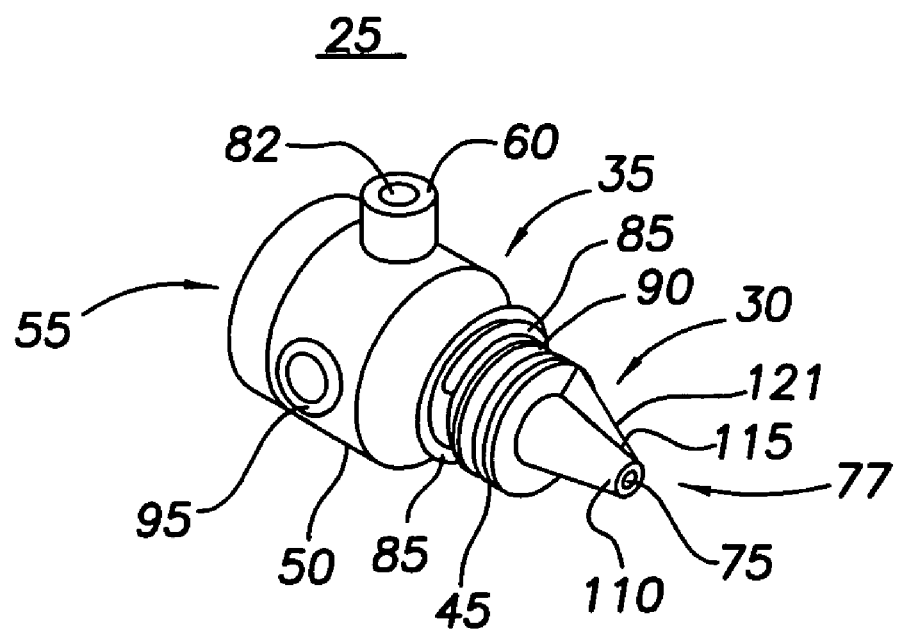
FIG. 14 is an isometric view of a hemostasis valve assembly with an integral slitting/splitting tool, wherein the tool employs a single blade.

In other embodiments, the slitting/splitting tool 30 will include a greater or lesser number of blades 115 than the embodiment depicted in FIGS. 1-6. For example, as shown in FIG. 14, in one embodiment, the slitting/splitting tool 30 includes a barrel portion 110 with a single blade 115 that extends perpendicularly from the outer circumferential surface of the barrel portion 110.

In one embodiment, the cylindrical body 50, the male connective end 45 and the slitting/splitting tool 30 are all formed from a generally rigid, hard material (e.g., acrylonitrile-butadiene-styrene "ABS", polyether block amides "PEBAX", high density polyethylene "HDPE", polycarbonate, nylon, etc.). In one embodiment, the blades 115 are integrally formed from the same polymer material as the body 50, end 45 and tool 30. In one embodiment, the blades 115 are inserts of other materials. For example, in one embodiment, the inserts forming the blades 115 are other types of polymers that have better sharp edge attributes. In one embodiment, the inserts forming the blades 115 are surgical steel or other types of metals having sharp edge attributes. In one embodiment, the inserts forming the blades 115 are ceramic or glass.

Figure 7:
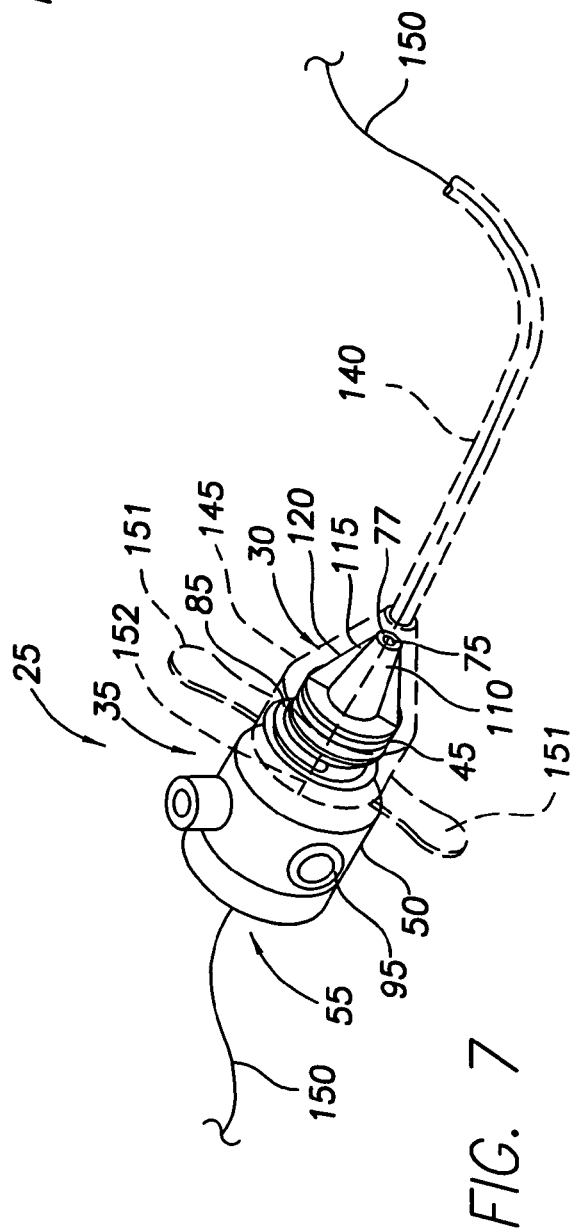
FIG. 7 is an isometric view of the hemostasis valve assembly of the subject invention coupled to a catheter or sheath tubular body via a female connector and wherein a medical device such as an LV lead extends through the valve assembly and the tubular body.
Figure 8:
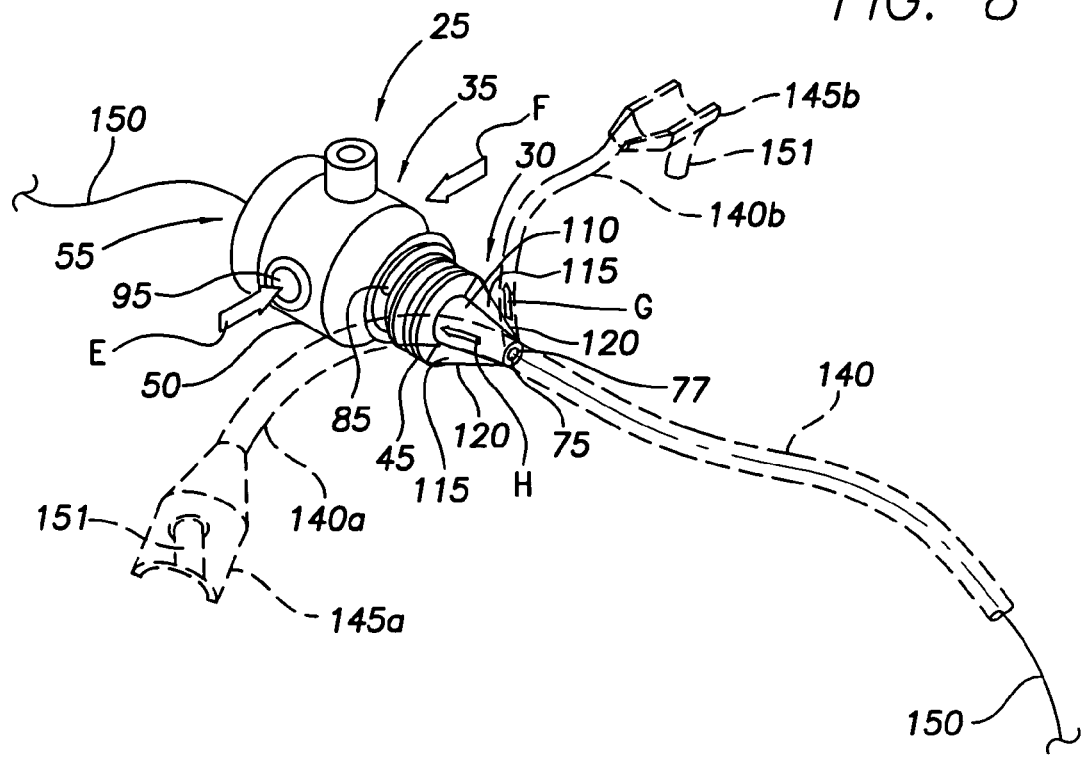
FIG. 8 is the same view depicted in FIG. 7, except the female connector has been split into halves and the slitting/splitting tool of the valve assembly is being used to slit/split the tubular body.

For a discussion of a method of employing the slitting/splitting tool 30 depicted in FIGS. 1-6, reference is made to FIGS. 7 and 8. FIG. 7 is an isometric view of the hemostasis valve assembly 25 of the subject invention coupled to a catheter or sheath tubular body 140 via a female connector 145 and wherein a medical device 150 such as an LV lead extends through the valve assembly 25 and the tubular body 140. FIG. 8 is the same view depicted in FIG. 7, except the female connector 145 has been split into halves 145a, 145b and the slitting/splitting tool 30 of the valve assembly 25 is being used to slit/split the tubular body 140.

As can be understood from FIG. 7, the tubular body 140 includes a female connective end 145 that is configured to matingly receive therein the male connective end 45 and the slitting/splitting tool 30. The connective ends 45, 145 are maintained together via the connective features (e.g., bayonet-type locks 85, threads, resilient clipping members, etc.) on the male connective end 45 mating with corresponding features on the female connective end 145.

As indicated in FIG. 7, in one embodiment, the female connective end 145 includes one or more grasping elements or wings 151 extending laterally outward from the exterior surface of the female connective end 145. The wings 151 serve as features that a user can grasp when coupling the female connective end 145 to the male coupling end 45 or when splitting/slitting the sheath tubular body 140.

As shown in FIG. 7, in one embodiment, the female connective end 145 also includes one or more pre-stressed or scored lines 152 running longitudinally along the length of the female connective end 145 to facilitate the splitting of the female connective end 145. In one embodiment, the female connective end 145 is split/slit along the pre-stressed lines 152 by grasping the wings 151 and forcing the wings 151 apart. In one embodiment, the female connective end 145 with its wings 151, pre-stressed line(s) 152 and attached tubular body 140 is as manufactured by St. Jude Medical, Inc. (One Lillehei Plaza, St. Paul, Minn. 55117) as part of the Apeel™ CS Catheter Delivery System, which is hereby incorporated by reference in its entirety.

The connection between the slitting/splitting tool 30 and the tubular body 140 is configured such that a fluid-tight seal is created to prevent air or other fluids from entering into or escaping from the lumens of the slitting/splitting tool 30 or tubular body 140 at the point of connection between the slitting/splitting tool 30 and the tubular body 140. For example, in one embodiment, the tip 77 mates with the tubular body 140 to form a fluid-tight seal that confines fluid to the lumens of the tubular body 140 and the slitting/splitting tool 30 while preventing air or other fluids from entering these same lumens from the surrounding ambient environment. In another embodiment, the barrel portion 110 mates with the female connector 145 to form a fluid-tight seal that confines fluid to the lumens of the tubular body 140 and the slitting/splitting tool 30 while preventing air or other fluids from entering these same lumens from the surrounding ambient environment.

As can be understood from FIGS. 5 and 7, the medical device 150 is inserted into the opening 70 of the entry end 55 of the valve assembly 25, through the slits in the membranes 80, 81, through the first lumen 65, out the opening 75 in the tip 77 of the tool 30, into the female connector 145, and through a lumen of the tubular body 140 to a treatment site within a patient. Thus, as shown in FIG. 7, the medical device 150 extends through the entire valve assembly 25 and tubular body 140.

As can be understood from FIG. 7, in one embodiment, the outer diameter of the tip 77 is generally equal to the outer diameter of the tubular body 140. Similarly, the inner diameter of the tip opening 75 is generally equal to the inner diameter of the tubular body 140.

As illustrated in FIG. 6, in one embodiment, the wall defining the conical barrel portion 110 tapers such that the wall at the tip 77 terminates as a relatively narrow edge that defines the tip opening 75. In one such embodiment, the outer diameter of the tip 77 is smaller than the outer diameter of the tubular body 140 and only slightly larger than the inner diameter of the tubular body 140, which is generally equal to the inner diameter of the tip opening 75.

As indicated in FIG. 8, to remove the tubular body 140 from about the medical device 150 without disturbing the medical device 150, the female connective end 145 of the tubular body 140 is manually split into halves 145a, 145b. In one embodiment, the female connective end 145 is manually split by utilizing a separate tool (e.g., surgical cutter, scalpel, saw, etc.) to cut the female connective end 145 prior to employing the blades 115 of the slitting/splitting tool 30 to cut the tubular body 140. In one embodiment the female connective end 145 is manually split by forcing the sidewalls of the female connective end 145 against the sharp cutting edges 120 of the blades 115. Depending on the embodiment, the sidewalls of the female connective end 145 can be brought sufficiently into cutting contact with the blades 115 by pressing the sidewalls of the female connective end 145 against the edges 120 of the blades 115. In other embodiments, the male and female connective ends are configured to sealingly mate, but still allow the female connective end 145 to selectively longitudinally rearwardly displace relative to the male connective end 45 such that the sidewalls of the female connective end 145 are brought into cutting contact with the blades 115.

In other embodiments, as previously mentioned with respect to FIGS. 7-8, the female connective end 145 is pre-stressed to split along a longitudinally extending line 152 in the female connective end 145 when a splitting force is applied to the female connective end 145. In one embodiment, the splitting force is applied to the wings 151 extending laterally from the female connective end 145. Specifically, the splitting force is applied to the wings 151 such that the wings 151, and their respective sides of the female connective end 145, are forced apart from each other, thereby causing the female connective end 145 to split along the lines 152.

In one embodiment, each pre-stress line 152 of a female connective end 145 is aligned with a cutting edge 120 of a blade 115 to facilitate the splitting of the female connective end 145. The female connective end 145 is displaced about the male connective end 45 towards the hemostasis valve 35 to bring each pre-stress line 152 into contact with a blade cutting edge 120, which causes the pre-stress line 152 of the female connective end 145 to split.

In one embodiment, in removing the female connective end 145 and tubular body 140 from about the medical device 150, the hemostasis valve assembly 25 is stabilized relative to the medical device 150 to prevent the medical device 150 from being dislodged from the patient. Depending on the embodiment of the tubular body removal process being employed, the stabilizing of the medical device 150 relative to the hemostasis valve 25 begins prior to, during, or shortly after the female connective end 145 is split/slit.

In one embodiment, the stabilizing component elements 95 (e.g., pads, depressible sections, buttons 95, resilient sidewalls of the cylindrical body 50, etc.) are squeezed inwardly such that the inner circumferential surface of the first lumen 65 is brought into engaging contact with the medical device 150. For example, where the stabilizing component is one or more buttons 95 having shafts 100 or other inwardly extending button portions, the shafts 100 or other button portions extend into the first lumen 65 when the buttons 95 are depressed (see FIG. 6). This causes the walls of the resilient lining or tube 105 to engage the sides of the medical device 150, thereby preventing displacement between the medical device 150 and the hemostasis valve assembly 25 as the tubular body 140 is being removed from about the medical device 150.

With the female connective end 145 split into halves 145a, 145b and the hemostasis valve assembly 25 fully engaged with the medical device 150 via the inward displacement of stabilizing component elements 95, as depicted by arrows E and F, the halves 145a, 145b are pulled proximally, as depicted by arrows G and H, with one hand while the other hand holds the valve assembly 25 in place such that the tubular body 140 is brought against the blades 115 of the slitting/splitting tool 30. This causes the tubular body 140 to slit/split open via the edges 120 of the blades 115, as depicted in FIG. 8. In one embodiment, where the tool 30 employs a single blade 115, the tubular body 140 will simply slit/split open. In one embodiment, where the tool 30 employs two blades 115, the tubular body 140 will slit/split into two halves or strips 140a, 140b. In one embodiment, where the tool 30 employs more than two blades 115, the tubular body 140 will slit/split into more than two strips.

As can be understood from FIG. 8, the tapered configuration of the conical barrel portion 110 and the tip 77 facilitates the slitting/splitting caused by the blades 115. The tapered configuration of the conical barrel portion 110 and the tip 77 causes the tubular body halves 140a, 140b to depart away from each other, as indicated in FIG. 8.

Once the full length of the tubular body 140 has been slit/split, the tubular body 140 can be removed from about the medical device 150. The hemostasis valve assembly 25 is then removed from about the medical device 150. In one embodiment, the hemostasis valve assembly 25 is removed from the medical device 150 by pulling the hemostasis valve assembly over the proximal end of the medical device 150. In another embodiment, the hemostasis valve assembly 25 is split and removed from the medical device 150.

Figure 9:
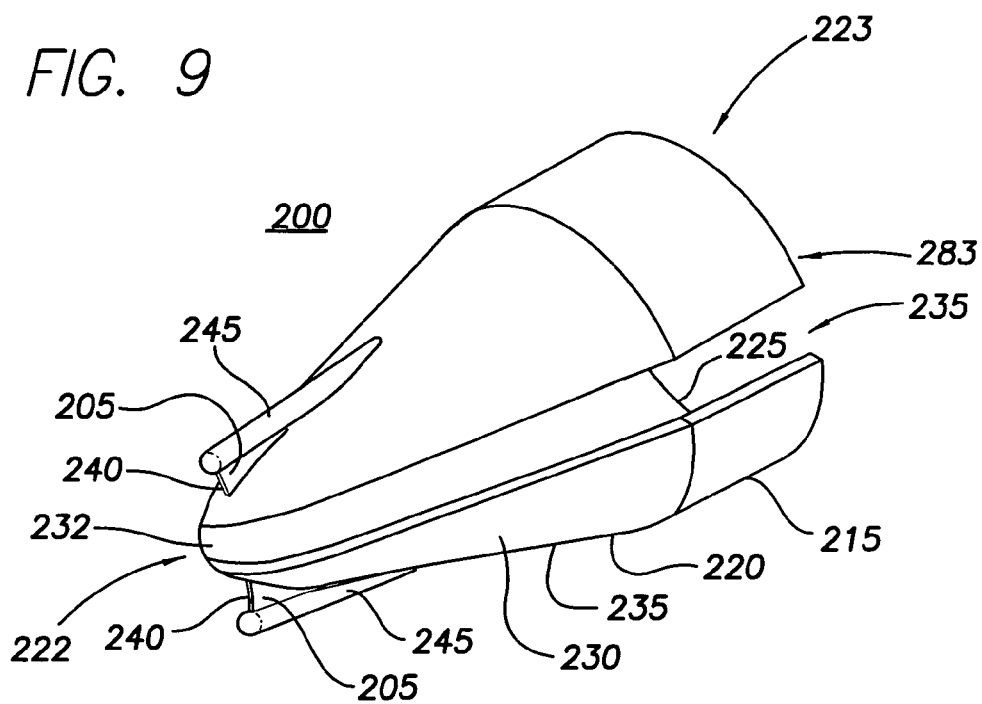
FIG. 9 is an isometric view of a slitting/splitting tool employing two blades and configured to be placed over a medical device and coupled to a hemostasis valve.
Figure 10:
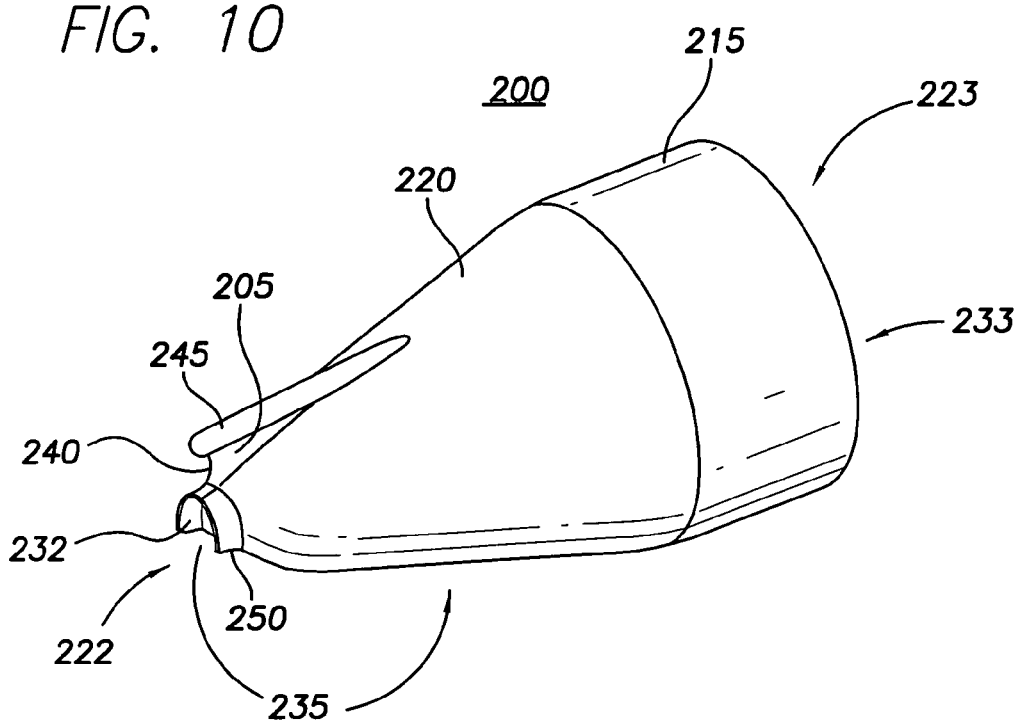
FIG. 10 is the same view depicted in FIG. 9, except of another embodiment of the slitting/splitting tool wherein the tool employs a single blade.
Figure 11:
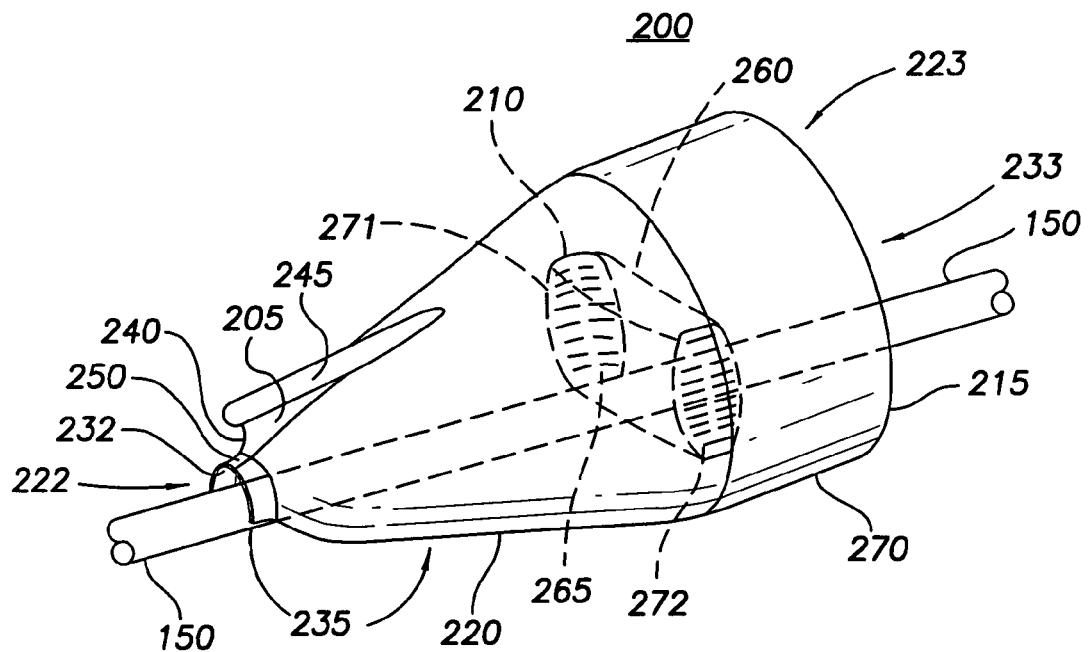
FIG. 11 is the same view depicted in FIG. 10, except of another embodiment of the slitting/splitting tool wherein the tool employs a medical device stabilizing component for resisting displacement between the tool and the medical device passing through the tool.

For a discussion regarding another embodiment of the subject invention, reference is made to FIGS. 9-11. FIG. 9 is an isometric view of a slitting/splitting tool 200 employing two blades 205 and configured to be placed over a medical device 150 and coupled to a hemostasis valve 35. FIG. 10 is the same view depicted in FIG. 9, except of another embodiment of the slitting/splitting tool 200 wherein the tool 200 employs a single blade 205. FIG. 11 is the same view depicted in FIG. 10, except of another embodiment of the slitting/splitting tool 200 wherein the tool 200 employs a medical device stabilizing component 210 for resisting displacement between the tool 200 and the medical device 150 passing through the tool 200.

As shown in FIG. 9, the slitting/splitting tool 200 includes a cylindrical barrel portion 215, a conical barrel portion 220, a tip 222 and a base 223. The conical barrel portion 220 extends forwardly from the cylindrical barrel portion 215 to terminate at the tip 222. The cylindrical barrel portion 215 extends rearward from the conical barrel portion 220 to terminate at the base 223.

In one embodiment, the cylindrical and conical barrel portions 215, 220 define, respectively, a cylindrical inner volume 225 and a conical inner volume 230. The tip 222 defines a tip opening 232 that leads into the conical inner volume 230. The base 223 defines a base opening 233 that leads into the cylindrical inner volume 225. In one embodiment, the tool 200 is formed from a generally rigid, hard material (e.g., ABS, PEBAX, HDPE, polycarbonate, nylon, etc.).

As illustrated in FIG. 9, the slitting/splitting tool 200 further includes a pair of blades 205 and a longitudinally extending slot 235. The longitudinal slot 235 extends through the sidewalls forming the cylindrical and conical barrel portions 215, 220 and from the tip opening 232 to the base opening 233. The longitudinal slot 235 allows the tool 200 to be placed over a medical device 150 to facilitate the slitting/splitting of a tubular body 140 extending about the medical device 150, as will be discussed later in this Detailed Description.

The blades 205 extend perpendicularly from opposite sides of the conical barrel portion 220 near the tip 222. Each blade 205 includes a forwardly facing sharp cutting edge 240. Each blade 205 is bounded along one longitudinally extending boundary by the surface of the conical barrel portion 220 and along the other longitudinally extending boundary by a cylindrical sheath guard 245. In other words, each blade 205 extends between a cylindrical sheath guard 245 and the surface of the conical barrel portion 220.

In one embodiment, the longitudinal axis of each cylindrical sheath guard 245 is generally parallel to the longitudinal axis of the slitting/splitting tool 200. As a result, the distance across the surface of a blade 205 between the cylindrical sheath guard 245 and the surface of the conical barrel portion 220 decreases traveling rearward from a blade's cutting edge 240.

In one embodiment, the blades 205 are integrally formed from the same polymer material as the rest of the tool 200. In one embodiment, the blades 205 are inserts of other materials. For example, in one embodiment, the inserts forming the blades 205 are other types of polymers that have better sharp edge attributes. In one embodiment, the inserts forming the blades 205 are surgical steel or other types of metals having sharp edge attributes. In one embodiment, the inserts forming the blades 205 are ceramic or glass.

While FIG. 9 depicts an embodiment of the slitting/splitting tool 200 that employs two blades 205, other embodiments will employ a greater or lesser number of blades 205. For example, as depicted in FIG. 10, the slitting/splitting tool 200 employs a single blade 205 that includes a cylindrical sheath guard 245. As can be understood from FIG. 10, the single blade 205 is positioned on the surface of the conical barrel portion 220 opposite from the location of the slot 235 that extends along the full length of the tool 200 as discussed above in reference to the tool 200 depicted in FIG. 9.

As illustrated in FIG. 10, in one embodiment, the conical barrel portion 215 terminates at a collar 250 that forms the tip 222 and defines the tip opening 232. In other embodiments, the tool 200 will employ a single blade 205, as depicted in FIG. 10, but will employ the tapered tip 222 depicted FIG. 9, as opposed to the collared tip 222 depicted in FIG. 10.

As shown in FIG. 11, in one embodiment, the slitting/splitting tool 200 includes a medical device stabilizing component 210 similar in effect to that discussed in reference to FIGS. 1-8. In one embodiment, the stabilizing component 210 shown in FIG. 11 employs the depressible sections 95 (e.g., pads, buttons 95, etc.), shafts 100 and resilient liner or tube 105 discussed in reference to FIGS. 1-8. In one embodiment, the stabilizing component 210 shown in FIG. 11 employs the resilient deflectable barrel sidewalls similar to those discussed in reference to FIGS. 1-8.

In one embodiment, as indicated in FIG. 11, the stabilizing component 210 is a resilient member 260 extending across the interior of the tool 200 and including a center slot 265 and first and second squeeze pads 270, 271. The center slot 265 is aligned with the longitudinal axis of the tool 200 and has an opening 272 that aligns with the longitudinally extending slot 235 to allow the medical device 150 to be received in the center slot 265 once the medical device has passes through the longitudinally extending slot 235. Each squeeze pad 270, 271 is a surface of the resilient member 260 that extends through the sidewall forming the cylindrical or conical barrel portions 215, 220. In one embodiment, the resilient member 260 and its components are formed from a generally resilient, soft polymer material (e.g., silicone, PEBAX, PBC, santaprene, neoprene, latex, etc.).

Depressing the squeeze pads 270, 271 inwardly compresses the resilient member 260 and causes the center slot 265 to distort (i.e., the diameter of the center slot 265 decreases) and engage the medical device 150 extending through the tool 200. Thus, the medical device stabilizing component 210 can be used to prevent displacement between the slitting/splitting tool 200 and the medical device 150. Not depressing the squeeze pads 270, 271 allows the center slot 265 to maintain its maximum diameter and, as a result, the tool 200 may freely displace along the medical device 150.

Figures 12, 13:
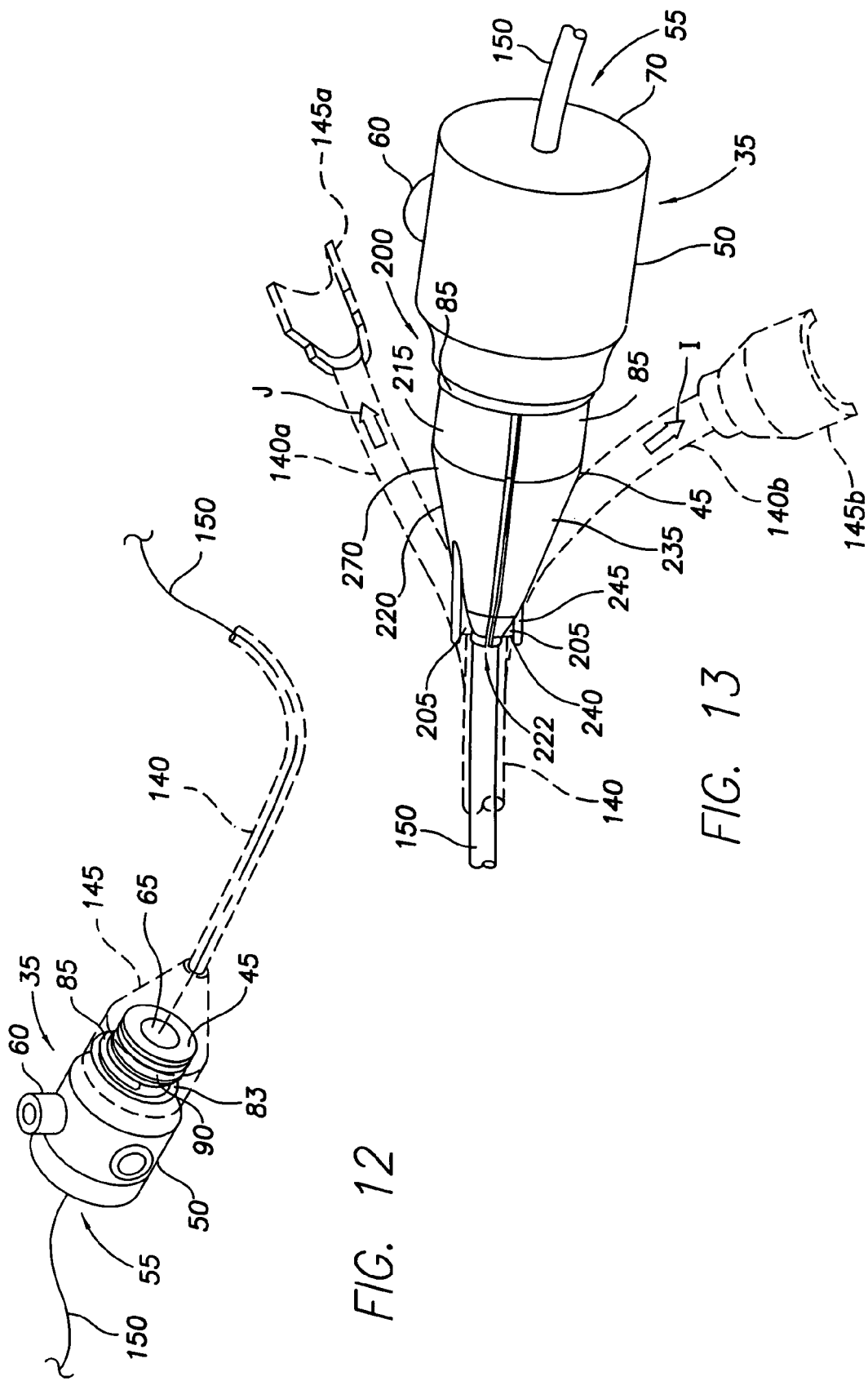
FIG. 12 is an isometric view of a hemostasis valve coupled to a catheter or sheath tubular body via a female connector and wherein a medical device such as an LV lead extends through the valve and the tubular body.
FIG. 13 is an isometric view of the slitting/splitting tool coupled to the hemostasis valve depicted in FIG. 12 and wherein the female connector has been split into halves and the slitting/splitting tool is being used to slit/split the tubular body.

For a discussion a method of employing the slitting/splitting tools 200 depicted in FIGS. 9-11, reference is made to FIGS. 12 and 13. FIG. 12 is an isometric view of a hemostasis valve 35 coupled to a catheter or sheath tubular body 140 via a female connector 145 and wherein a medical device 150 such as an LV lead extends through the valve 35 and the tubular body 140. FIG. 13 is an isometric view of the slitting/ splitting tool 200 coupled to the hemostasis valve 35 depicted in FIG. 12 and wherein the female connector 145 has been split into halves 145a, 145b via a separate slitting/splitting tool or via the tool 200 itself, and the slitting/splitting tool 200 is being used to slit/split the tubular body 140.

As shown in FIG. 12, the tubular body 140 includes a female connective end 145 that is configured to matingly receive therein the male connective end 45. The connective ends 45, 145 are maintained together via the bayonet-type locks 85 (or other mechanical coupling features such as threads, resilient or biased clipping arrangements, etc.) on the male connective end 45 mating with corresponding features on the female connective end 145. FIGS. 12 and 13 depict the hemostasis valve 35 as having a male connective end 45 and the tubular body 140 as having a female connective end 145. However, those skilled in the art will understand that the location of the male and female connective ends could be reversed and the following method of slitting/splitting the tubular body 140 with the tool 200 would remain generally the same.

As can be understood from FIG. 12 and in a manner similar to that discussed in reference to FIGS. 1-8, the medical device 150 is inserted into the opening of the entry end 55 of the hemostasis valve 35, through the valve 35, into the female connector 145, and through a lumen of the tubular body 140 to a treatment site within a patient. Thus, as shown in FIG. 12, the medical device 150 extends through the entire hemostasis valve 35 and tubular body 140.

As can be understood from FIGS. 9 and 11-13, to remove the tubular body 140 from about the medical device 150 without disturbing the medical device 150, the female connective end 145 of the tubular body 140 is manually split into halves 145a, 145b. A proximal portion of the tubular body 140 immediately distal the female connector 145 is also slit/split to expose a segment of the medical device 150. The slitting/splitting tool 200 is placed over the exposed segment of the medical device 150 via the longitudinally extending slot 235 (see FIG. 9) such that the medical device 150 is received within the opening 272 of the center slot 265 in the resilient member 260 (see FIG. 11). The base opening 233 is placed over, and coupled to, the male connective end 45. The tool 200 and valve 35 now appear as shown in FIG. 13 with the medical device 150 extending longitudinally through the tool 200 and the hemostasis valve 35.

In one embodiment, coupling between the tool 200 and valve 35 is achieved via bayonet-type features on the base 223 of the tool 200 engaging with the bayonet-type connectors 85 on the male connective end 45 of the hemostasis valve 35. In one embodiment, coupling is achieved via a lip or groove extending about the inner circumferential surface of the base opening 233 engaging with one or more of the flanges radially extending about the male connective end 45 of the valve 35. Securing the valve 35 and tool 200 together into one continuous unit provides an elongated gripping surface, which makes it easier for a user to grip the valve 35 and tool 200 when removing a tubular body 140 from about a medical device 150.

As can be understood from FIGS. 11 and 13, the squeeze pads 270, 271 on the slitting/splitting tool 200 are squeezed inwardly. This causes the center slot 265 to distort such that its diameter decreases to engage the sides of the medical device 150, thereby preventing displacement between the medical device 150 and the combined hemostasis valve 35 and tool 200 as the tubular body 140 is being removed from about the medical device 150.

With the female connective end 145 split into halves 145a, 145b and the combined hemostasis valve 35 and tool 200 fully engaged with the medical device 150 via the inward displacement of the squeeze pads 270, 271, the halves 145a, 145b are pulled proximally, as depicted by arrows I and J, with one hand while the combined valve 35 and tool 200 are held in place such that the tubular body 140 is brought against the blades 205 of the slitting/splitting tool 200. This causes the tubular body 140 to slit/split open via the edges 240 of the blades 205, as depicted in FIG. 13.

In one embodiment, as depicted in FIGS. 10 and 11, where the tool 200 employs a single blade 205, the tubular body 140 will simply slit/split open. In one embodiment, as depicted in FIGS. 9 and 13, where the tool 200 employs two blades 205, the tubular body 140 will slit/split into two halves or strips 140a, 140b.

As can be understood from FIG. 13, the tapered configuration of the conical barrel portion 220 and the tip 222 facilitates the slitting/splitting caused by the blades 205. The tapered configuration of the conical barrel portion 220 and the tip 222 causes the tubular body halves or strips 140a, 140b to depart away from each other, as indicated in FIG. 13.

Once the full length of the tubular body 140 has been slit/split, the tubular body 140 is removed from about the medical device 150, and the tool 200 is removed from the hemostasis valve 35 and medical device 150 via the slot 235. The hemostasis valve 35 is then removed from about the medical device 150. In one embodiment, the hemostasis valve 35 is removed from about the medical device 150 by pulling the hemostasis valve 35 over the proximal end of the medical device 150. In another embodiment, the hemostasis valve 35 is split and removed from about the medical device 150.

Although the present invention has been described with reference to preferred embodiments, persons skilled in the art will recognize that changes may be made in form and detail without departing from the spirit and scope of the invention.

What is claimed is:

1. A catheter/sheath system comprising:
   a hemostasis valve having a proximal portion and a distal portion;
   a slitting/splitting tool extending from the distal portion of the hemostasis valve, the slitting/splitting tool having a blade with an edge that extends along a route that is generally parallel to a longitudinal axis of the hemostasis valve; and
   an elongated tubular body having a proximal portion and a distal portion, the proximal portion of the elongated tubular body coupled to the distal portion of the hemostasis valve;
   wherein the elongated tubular body is disposed distal to the slitting/splitting tool, and wherein the slitting/splitting tool longitudinally cuts the elongated tubular body to facilitate removal of the elongated tubular body from about a medical device extending through the hemostasis valve and elongated tubular body; and
   wherein the slitting/splitting tool is coupled to the hemostasis valve via chemical, sonic, laser, or heat welding.

2. The system of claim 1, further comprising a slot extending longitudinally along the slitting/splitting tool.

3. The system of claim 1, further comprising a conical barrel portion at the distal portion of the hemostasis valve.

4. The system of claim 3, wherein the blade extends radially outward from the conical barrel portion.

5. The system of claim 1, wherein the edge extends along a route that is generally oblique to a longitudinal axis of the slitting/splitting tool.

6. The system of claim 1, wherein a distance between the edge and a longitudinal axis of the slitting/splitting tool increases as the edge is followed rearwardly from a front tip of the slitting/splitting tool.

7. The system of claim 1, wherein the edge extends along a route that is generally parallel to a longitudinal axis of the tool.

8. The system of claim 1, wherein the blade further comprises a guard that longitudinally extends along a radially outward border of the blade.

9. The system of claim 1, further comprising a stabilizing component adapted to selectively resist displacement between the slitting/splitting tool and the medical device.

10. The system of claim 1, wherein a front tip of the slitting/splitting tool mates with the elongated tubular body to form a fluid-tight seal.

11. The system of claim 1, further comprising a male connector and a female connector, the male connector located at the distal portion of the hemostasis valve, the female connector detachably mating with the male connector, a distal portion of the female connector coupled to the proximal portion of the elongated tubular body to form a fluid-tight seal.

12. The system of claim 1, wherein the medical device is an implantable lead for a cardiac stimulation device.

\* \* \* \* \*

UNITED STATES PATENT AND TRADEMARK OFFICE
CERTIFICATE OF CORRECTION

PATENT NO.        : 7,632,254 B1                                              Page 1 of 1
APPLICATION NO.   : 11/338031
DATED             : December 15, 2009
INVENTOR(S)       : Bjorkman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 545 days.

Signed and Sealed this

Second Day of November, 2010

David J. Kappos
*Director of the United States Patent and Trademark Office*